US00PP11991P2

(12) United States Plant Patent
Flint

(10) Patent No.: US PP11,991 P2
(45) Date of Patent: Jul. 17, 2001

(54) CHRYSANTHEMUM PLANT NAMED 'ROSE DELANO'

(75) Inventor: David B. Flint, Buhl, ID (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,533

(22) Filed: Aug. 26, 1999

(51) Int. Cl.[7] ..... A01H 5/00
(52) U.S. Cl. ..... Plt./287
(58) Field of Search ..... Plt./287, 293

*Primary Examiner*—Howard J. Locker

(74) *Attorney, Agent, or Firm*—C. A. Whealy

(57) ABSTRACT

A distinct cultivar of Chrysanthemum plant named 'Rose Delano', characterized by its upright, outwardly spreading and uniformly mounded plant habit; freely branching habit, full and dense plants; large dark green leaves; uniform flowering; early flowering, eight-week response time; large decorative-type inflorescences that are about 11.5 cm in diameter; the ray floret color of plants of the new Chrysanthemum can range from a cream yellow at the base with dark purple-colored apices to mostly cream yellow with occasional dark purple flecking; and good to excellent postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandifora* and hereinafter referred to by the cultivar name Rose Delano.

The new Chrysanthemum was discovered by the Inventor in a controlled environment in Layton, Utah in 1995, as a naturally-occurring mutation of the *Dendranthema grandifora* 'Spring Delano', disclosed in U.S. Plant Pat. No. 9,843. The new Chrysanthemum was observed as a single plant in a group of flowering plants of the parent cultivar. The selection of this plant was based on its different ray floret color.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Rose Delano has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rose Delano'. These characteristics in combination distinguish 'Rose Delano' as a new and distinct Chrysanthemum:

1. Upright, outwardly spreading and uniformly mounded plant habit.

2. Freely branching habit, full and dense plants.

3. Large dark green leaves.

4. Uniform flowering.

5. Early flowering, eight-week response time.

6. Large decorative-type inflorescences that are about 11.5 cm in diameter.

7. The ray floret color of plants of the new Chrysanthemum can range from a cream yellow at the base with dark purple-colored apices to mostly cream yellow with occasional dark purple flecking.

8. Good to excellent postproduction longevity with inflorescences and leaves maintaining good substance and color for about three weeks in an interior environment.

Compared to plants of the parent cultivar, Spring Delano, plants of the new Chrysanthemum differ in ray floret color and inflorescence size.

Compared to plants of the cultivar Red Delano, disclosed in U.S. Plant Pat. No. 8,345, plants of the new Chrysanthemum have slightly larger inflorescences and differ in ray floret color.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Rose Delano'.

The photograph at the bottom of the first sheet comprises a close-up view of a typical inflorescence and upper (left) and lower (right) surfaces of typical leaves of the cultivar Rose Delano.

The photograph at the top of the second sheet comprises a side perspective view of typical flowering plants of 'Rose Delano' (left) and 'Red Delano' (right).

The photograph at the bottom of the second sheet comprises a close-up view of typical inflorescences of plants of 'Rose Delano' (left) and 'Red Delano' (right). Floret and foliage colors in the photographs may appear different from the actual colors due to light reflectance.

DETAILED BOTANICAL DESCRIPTION

In the following description, color references are made to The Royal Horticultural Society Colour Chart exept where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Rose Delano.

Commercial classification: Decorative disbudded-type pot Chrysanthemum.

Parentage: Naturally-occurring mutation of *Dendranthema grandiflora* cultivar Spring Delano, disclosed in U.S. Plant Pat. No. 9,843.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative pot Chrysanthemum typically grown as a disbudded-type. Inverted triangle; upright and outwardly spreading giving a uniformly mounded appearance to the plant. Freely branching; about four lateral branches develop after removal of terminal apex (pinching); dense and full plants.

*Plant height.*—About 30 cm.

*Plant width.*—About 41 cm.

*Stem texture.*—Pubescent.

*Stem color.*—144A.

*Foliage description.*—Arrangement: Alternate. Length: About 8.5 cm. Width: About 6.7 cm. Apex: Cuspidate. Base: Truncate. Margin: Palmately lobed, sinuses between lateral lobes mostly parallel. Texture: Upper and lower surfaces with very fine pubescence; veins prominent on lower surface. Petiole length: About 2.1 cm. Petiole diameter: About 3 mm. Color: Young foliage upper surface: 147A. Young foliage lower surface: 147B. Mature foliage upper surface: 147A. Mature foliage lower surface: 147B. Venation upper surface: Close to 147B. Venation lower surface: 147B.

Inflorescence description:

*Appearance.*—Decorative inflorescence form with elongated-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later.

*Postproduction longevity.*—Inflorescences and leaves will maintain good color and substance for about three weeks in an interior environment.

*Quantity of Inflorescences.*—As a disbudded-type, all lateral inflorescences are removed to allow for maximum terminal inflorescence size. One inflorescence per lateral stem; about four inflorescences per plant.

*Inflorescence bud.*—Height: About 6.5 mm. Diameter: About 8 mm. Color: Close to 143A.

*Inflorescence size.*—Diameter: About 11.5 cm. Depth (height): About 3.5 cm. Diameter of disc: About 7 mm, inconspicuous.

*Ray florets.*—Shape: Narrowly elliptic. Orientation: Initially upright, then mostly perpendicular to peduncle; incurved. Aspect: Concave. Length: About 6.5 cm. Width: About 1.7 cm. Apex: Rounded to emarginate. Margin: Entire. Texture: Satiny, smooth, ridged longitudinally. Number of ray florets per inflorescence: About 168. Color: When opening: Dark purple, close to 58A towards apices; base, 8B. Fully opened, upper surface: 8C. Fully opened, lower surface: 8C to 8D; occasional dark purple, 58A to 58B, flecking.

*Disc florets.*—Shape: Tubular. Apex: Serrated. Length: About 8 mm. Width: Apex, about 1.5 mm; base, about 1 mm. Number of disc florets per inflorescence: Few, about 24. Color: Immature: 144A to 154A. Mature: Apex: 9A. Mid-section and base: White, 155D.

*Reproductive organs.*—Androecium: Present on disc florets only. Anther color: 17A. Pollen amount: Scarce. Pollen color: 17A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Rose Delano', as illustrated and described.

* * * * *

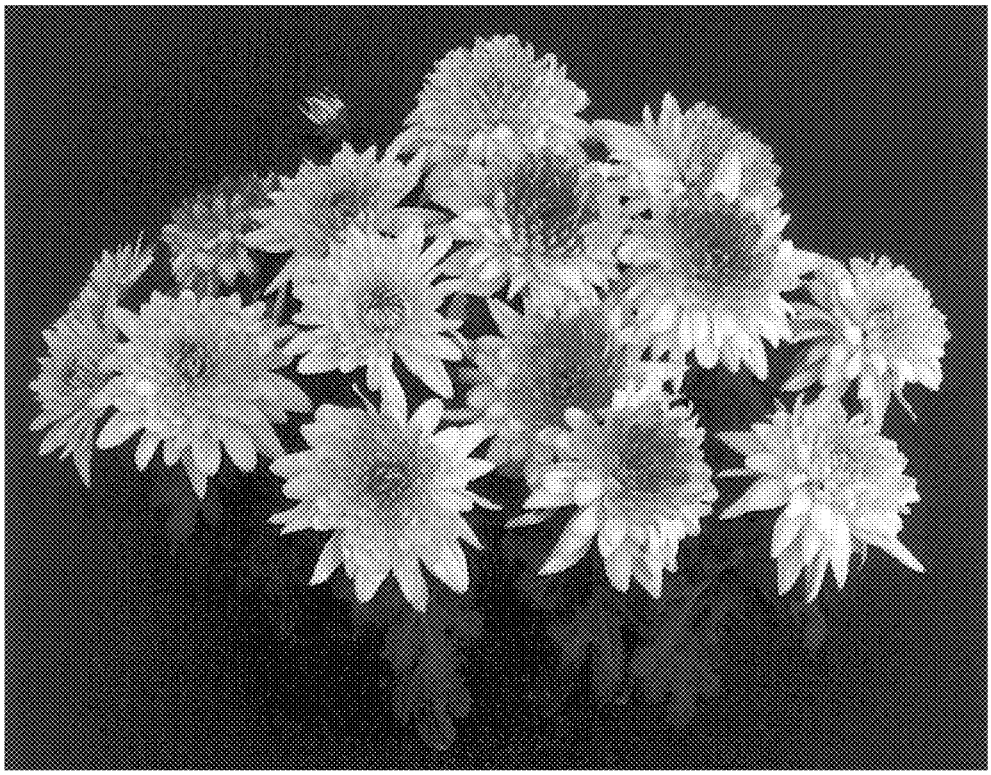
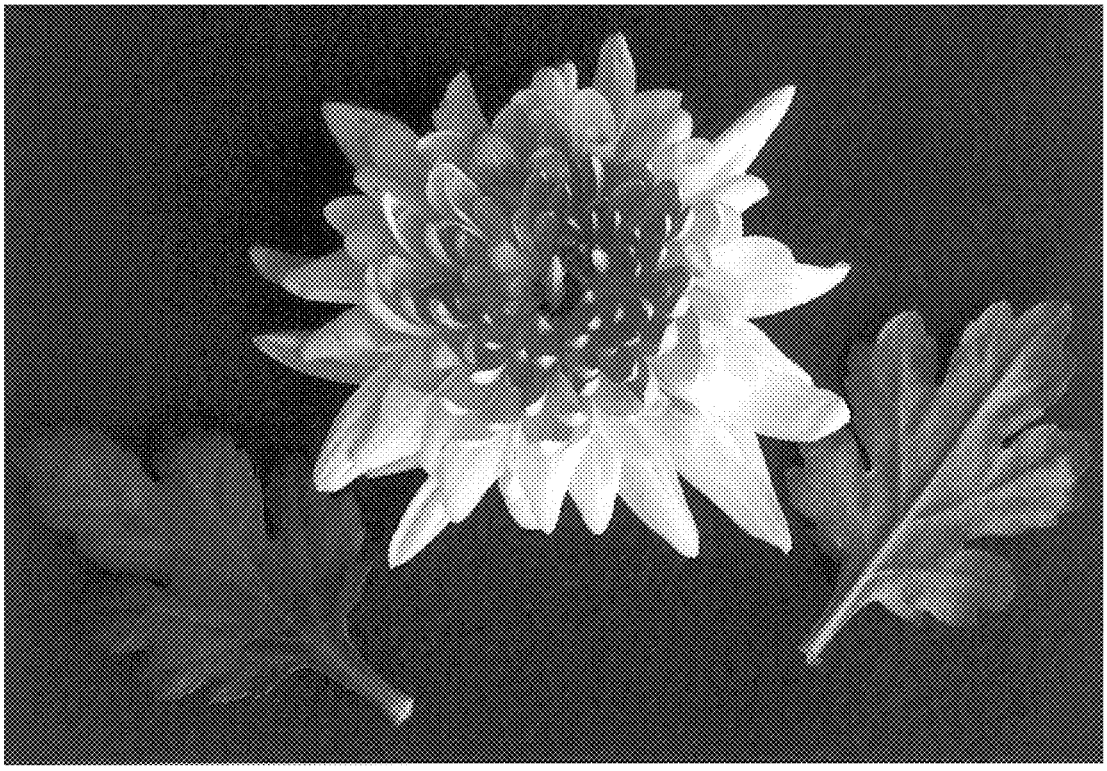

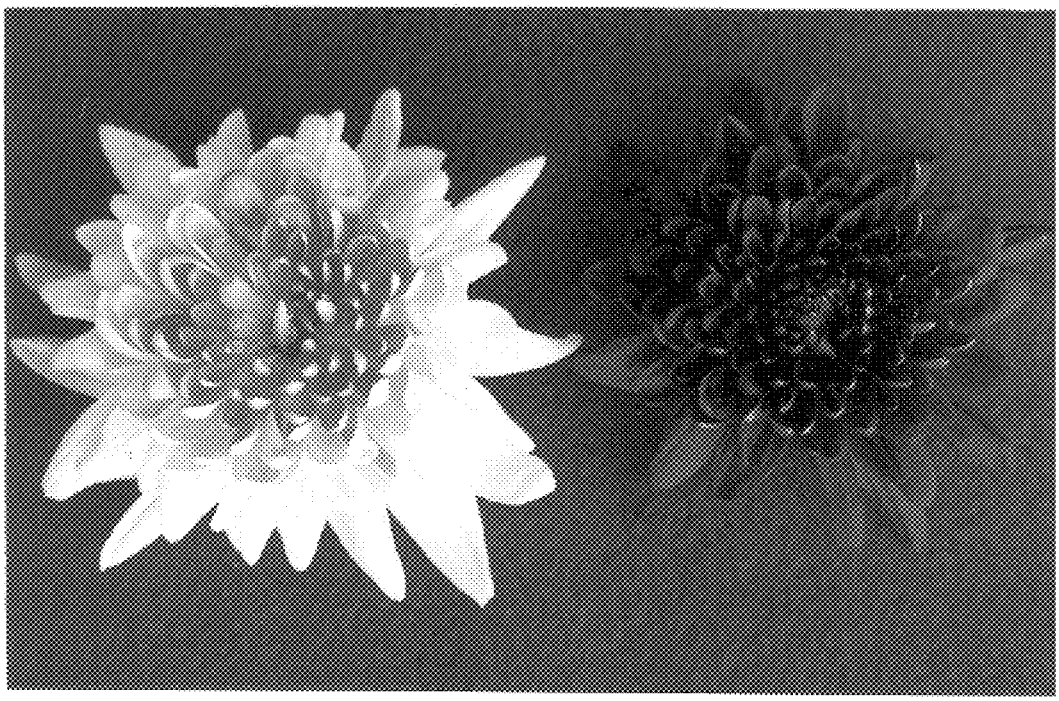

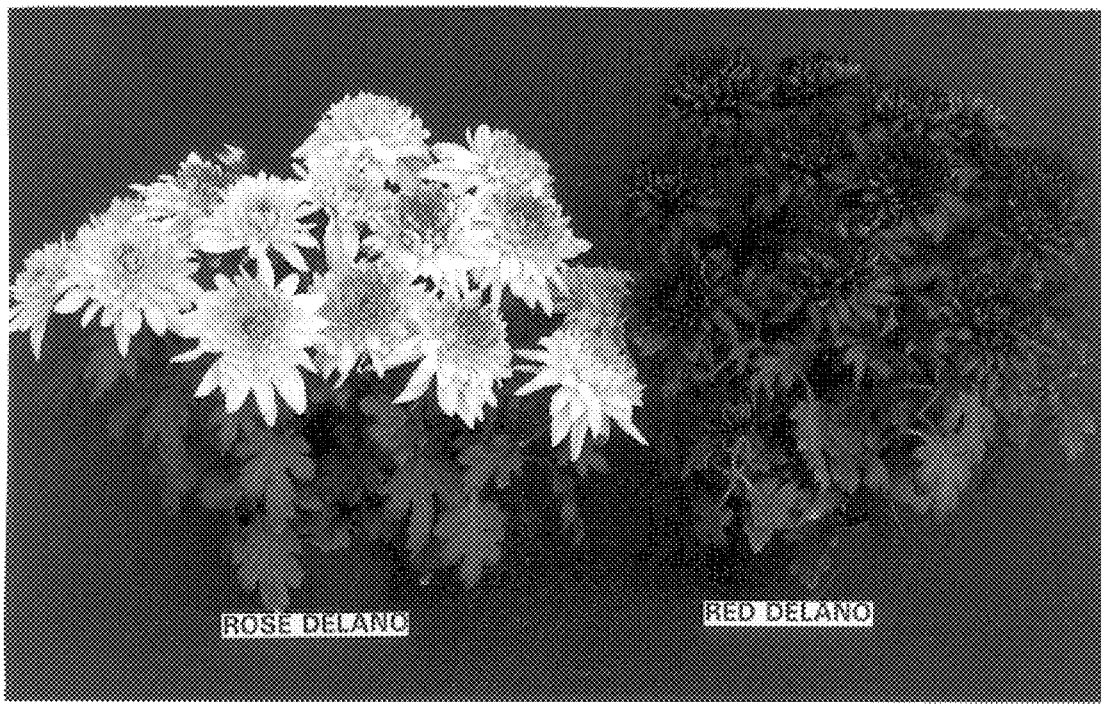
ROSE DELANO
RED DELANO